United States Patent
Giles et al.

(10) Patent No.: US 9,939,407 B2
(45) Date of Patent: Apr. 10, 2018

(54) ION MOBILITY SEPARATION DEVICE WITH MOVING EXIT APERTURE

(71) Applicant: Micromass UK Limited, Wilmslow (GB)

(72) Inventors: Kevin Giles, Stockport (GB); Jason Lee Wildgoose, Stockport (GB)

(73) Assignee: Micromass UK Limited, Wilmslow (GB)

( * ) Notice: Subject to any disclaimer, the term of this patent is extended or adjusted under 35 U.S.C. 154(b) by 0 days.

(21) Appl. No.: 14/367,585

(22) PCT Filed: Dec. 21, 2012

(86) PCT No.: PCT/GB2012/053256
§ 371 (c)(1),
(2) Date: Jun. 20, 2014

(87) PCT Pub. No.: WO2013/093515
PCT Pub. Date: Jun. 27, 2013

(65) Prior Publication Data
US 2014/0312222 A1 Oct. 23, 2014

Related U.S. Application Data

(60) Provisional application No. 61/580,538, filed on Dec. 27, 2011.

(30) Foreign Application Priority Data

Dec. 23, 2011 (GB) .................................. 1122267.6

(51) Int. Cl.
*G01N 27/62* (2006.01)
*H01J 49/06* (2006.01)

(52) U.S. Cl.
CPC .......... *G01N 27/622* (2013.01); *H01J 49/062* (2013.01)

(58) Field of Classification Search
CPC ........ H01J 49/06; H01J 49/062; G01N 27/62; G01N 27/062
See application file for complete search history.

(56) References Cited

U.S. PATENT DOCUMENTS 5,227,628 A 7/1993 Turner
5,324,939 A * 6/1994 Louris et al. ................ 250/292
(Continued)

OTHER PUBLICATIONS

Clemmer et al., "*High Resolution Ion Cyclotron Mobility Spectrometry*", Anal. Chem., vol. 81, pp. 1482-1487, 2009.

*Primary Examiner* — Wyatt Stoffa
*Assistant Examiner* — Sean Luck

(57) ABSTRACT

A method and device for separating ions according to their ion mobility are disclosed. An ion guide is provided having a plurality of electrodes arranged to form an ion guiding path that extends in a closed loop. RF voltages are supplied to at least some of the electrodes in order to confine ions within said ion guiding path. A DC voltage gradient is maintained along at least a portion of a longitudinal axis of said ion guide, wherein the voltage gradient urges ions along the ion guide such that the ions separate according to their ion mobility as the ions pass along the ion guide. As time progresses the portion of the ion guide along which the DC voltage gradient is maintained is moved along the ion guide. An ion exit region is provided which moves around said ion guide such that ions exit said ion guide at different locations at different times. The present invention allows ions to exit the ion guide after the ions have been separated and without having to wait until the ions reach a fixed exit point, by which time the ions may re-merge with other ions.

36 Claims, 5 Drawing Sheets

(56) References Cited

U.S. PATENT DOCUMENTS

| | | | |
|---|---|---|---|
| 6,674,071 B2* | 1/2004 | Franzen et al. | 250/292 |
| 6,753,522 B2* | 6/2004 | Guevremont et al. | 250/287 |
| 7,041,969 B2* | 5/2006 | Guevremont et al. | 250/285 |
| 7,385,187 B2* | 6/2008 | Verentchikov | H01J 49/406 |
| | | | 250/281 |
| 7,482,582 B2 | 1/2009 | Raznikov et al. | |
| 7,838,821 B2 | 11/2010 | Clemmer et al. | |
| 7,872,228 B1* | 1/2011 | Kim et al. | 250/292 |
| 7,947,948 B2* | 5/2011 | Schwartz | 250/283 |
| 8,067,747 B2 | 11/2011 | Wollnik | |
| 8,362,420 B2 | 1/2013 | Clemmer et al. | |
| 8,415,618 B2 | 4/2013 | Hoyes | |
| 8,440,967 B2 | 5/2013 | Giles | |
| 8,829,464 B2 | 9/2014 | Hayes et al. | |
| 9,177,776 B2 | 11/2015 | Hoyes et al. | |
| 2003/0001088 A1* | 1/2003 | Bateman et al. | 250/287 |
| 2005/0151076 A1* | 7/2005 | Yamaguchi et al. | 250/291 |
| 2006/0289746 A1* | 12/2006 | Raznikov et al. | 250/294 |
| 2008/0006768 A1* | 1/2008 | Yamaguchi | 250/287 |
| 2009/0014641 A1* | 1/2009 | Bateman et al. | 250/282 |
| 2009/0206250 A1* | 8/2009 | Wollnik | 250/290 |
| 2009/0272891 A1* | 11/2009 | Giles | 250/282 |
| 2010/0193678 A1* | 8/2010 | Clemmer et al. | 250/282 |
| 2011/0042563 A1* | 2/2011 | Giles | 250/286 |

\* cited by examiner

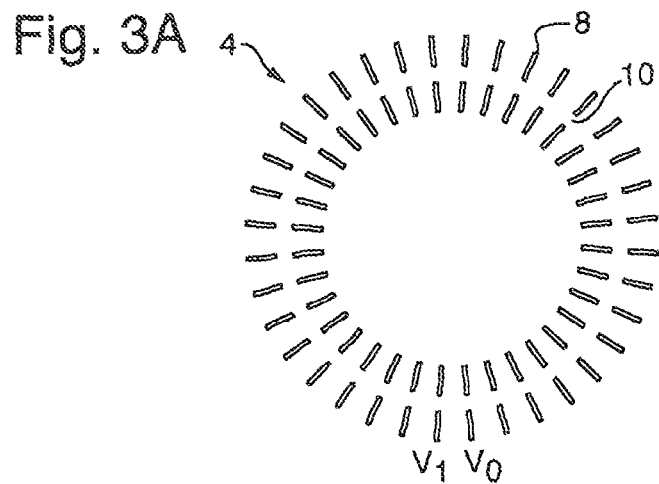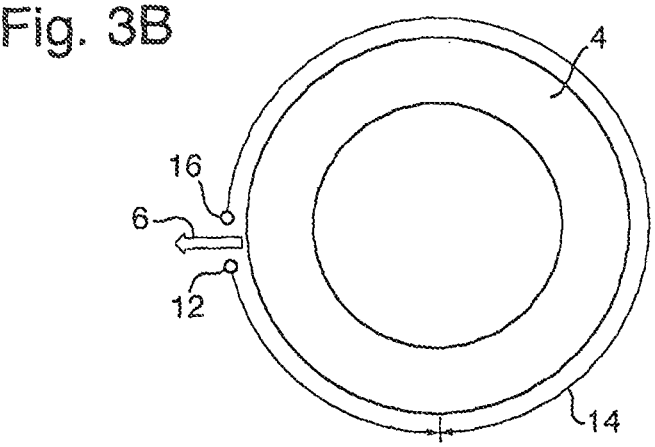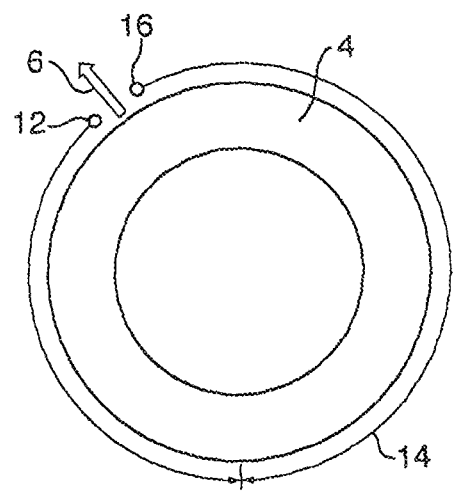

ION MOBILITY SEPARATION DEVICE WITH MOVING EXIT APERTURE

CROSS-REFERENCE TO RELATED APPLICATION

This application is the National Stage of International Application No. PCT/GB2012/053256, filed 21 Dec. 2012, which claims priority from and the benefit of U.S. Provisional Patent Application Ser. No. 61/580,538 filed 27 Dec. 2011 and United Kingdom Patent Application No. 1122267.6 filed on 23 Dec. 2011. The entire contents of this application is incorporated herein by reference.

BACKGROUND OF THE PRESENT INVENTION

It is known to apply a uniform electric field across a drift region of an ion mobility spectrometer (IMS) in order to separate ions according to their ion mobilities. It is desirable to provide such devices with relatively high resolution. It is possible to increase the resolution of such a device by increasing the electric field strength in the drift region. However, this will ultimately result in electrical breakdown in the drift gas. In order to increase the resolution of the device it is therefore conventionally considered necessary to increase the length of the drift region, whilst maintaining the electric field strength. However, this leads to a relatively long IMS device and the use of a larger potential difference in order to maintain the same electric field strength over the longer drift region. This necessitates the use of high absolute voltages, which may result in hazardous electrical discharges to the surrounding areas.

It is therefore desired to provide an improved ion mobility separator and an improved method of separating ions according to their ion mobility.

SUMMARY OF THE PRESENT INVENTION

The present invention provides a method of separating ions according to their ion mobility comprising:

providing an ion guide having a plurality of electrodes arranged to form an ion guiding path;

supplying RF voltages to at least some of said electrodes in order to confine ions within said ion guiding path;

maintaining a DC voltage gradient along at least a portion of a longitudinal axis of said ion guide, wherein said voltage gradient urges ions along the ion guide such that they separate according to their ion mobility as they pass along the ion guide, and wherein as time progresses the portion of the ion guide along which the DC voltage gradient is maintained is moved along the ion guide; and providing an ion exit region which moves along said ion guide such that ions exit said ion guide at different locations at different times.

As the exit region moves along the ion guide in the present invention, ions can exit the ion guide at the optimum time during their separation process. For example, ions may separate as the move along the DC voltage gradient and it may be desirable for the ions to exit the ion guide at the time that they reach an end of the voltage gradient, since this may be the point in time that the ions are at their optimum separation from other ions. This is in contrast to ion mobility separation methods wherein the ion exit region is at a fixed location. In such methods, ions may separate from other ions before they reach the exit region, but may re-merge with the other ions by the time that they reach the exit region.

Preferably, the method comprises moving the voltage gradient along the ion guide in a direction corresponding to the direction from high to low potential of the voltage gradient.

The DC voltage gradient and exit region may be moved along the ion guide with time such that the exit region remains at the low potential end of the voltage gradient so that ions exit the ion guide when they reach the low potential end of the voltage gradient.

According to one set of embodiments, the method comprises providing a potential barrier, preferably a DC barrier, at the high potential end of the voltage gradient for preventing ions from exiting the voltage gradient region from the high potential end of the voltage gradient as the voltage gradient is moved along the ion guide. The method may comprise moving the voltage gradient along the ion guide at a first, high speed such that ions reside adjacent to the potential barrier and do not move down the voltage gradient, and then reducing the speed at which the voltage gradient is moved along the ion guide to a second, low speed such that ions move down the voltage gradient away from the potential barrier and separate according to ion mobility. When the voltage gradient is moving at said first, high speed, ions of high and low ion mobility may be forced to reside adjacent to said potential barrier and when the voltage gradient is moving at said second, low speed, ions of low ion mobility may be forced to reside adjacent to said potential barrier, but ions of high mobility may move down said voltage gradient and separate according to ion mobility. The method may further comprise reducing the speed at which the voltage gradient is moving around the ion guide to a third speed that is lower than said second speed such that said low mobility ions move down the voltage gradient and separate according to ion mobility. The ion guide preferably forms a closed loop ion guiding path, and the speed of the voltage gradient is selected such that said high and/or low mobility ions are driven multiple cycles around the ion guide whilst they travel down the voltage gradient.

The speed of the voltage gradient may be changed in a continuous manner or it may be changed in a stepped manner. The speed of the voltage gradient may be changed in a linear or non-linear manner.

According to an alternative set of embodiments, the method comprises providing a potential barrier, preferably a DC barrier, at the low potential end of the voltage gradient for preventing ions from exiting the voltage gradient region from the low potential end of the voltage gradient. The method may comprise maintaining the voltage gradient stationary or moving the voltage gradient along the ion guide at a first, low speed such that ions are forced in a direction towards the potential barrier by the voltage gradient, and then increasing the speed at which the voltage gradient is moved along the ion guide to a second, high speed such that ions move up the voltage gradient and begin to separate according to ion mobility. When the voltage gradient is stationary or moving at said first, low speed, ions of high and low ion mobility may be forced to reside adjacent to said potential barrier. When the voltage gradient is moving at said second, high speed, ions of high ion mobility may be forced to reside adjacent to said potential barrier, but ions of low mobility may move up said voltage gradient towards the high potential end and separate according to ion mobility. The method preferably further comprises increasing the speed at which the voltage gradient is moved around the ion guide to a third speed that is higher than said second speed such that said high mobility ions move up the voltage gradient and begin to separate according to ion mobility. The ions guide preferably forms a closed loop ion guiding path, and the speed of the voltage gradient may be selected such that said high and/or low mobility ions are driven multiple cycles around the ion guide whilst they travel up the voltage gradient. The exit region preferably moves along the ion guide such that it is maintained at a high potential end of the voltage gradient, and the ions move up the voltage gradient and exit the ion guide at the high potential end.

The speed of the voltage gradient may be changed in a continuous manner or it may be changed in a stepped manner. The speed of the voltage gradient may be changed in a linear or non-linear manner.

According to the present invention, the exit region is preferably formed over a portion of said ion guide by modifying a voltage supplied to one or more of said electrodes such that ions are not confined by said one or more electrodes in the exit region. A first potential may be applied to the electrodes outside of the exit region in order to radially confine ions and a second, different potential may be applied to one or more electrodes inside the exit region in order to allow or cause ions to exit the ion guide. The second potential is preferably sequentially applied to successive electrodes along the ion guide such that the exit region moves along the ion guide.

According to the present invention, the plurality of electrodes preferably comprise apertured electrodes, and the electrodes and apertures of the electrodes are preferably aligned so as to guide ions through the apertures and around the ion guide. The aperture in each apertured electrode may be a slot formed into the electrode from an edge thereof, such that the slot has an open end at an edge of the electrode. At least one gate electrode may be provided adjacent to the open end of each slot, and a first potential may be applied to the gate electrode in order to prevent ions exiting the open end of the slot in regions of the ion guide outside of the exit region. A second potential may be applied to the gate electrode in order to allow or cause ions to exit the open end of the slot in regions of the ion guide inside of the exit region. The electrodes are preferably arranged such that at least a portion of the ion guiding path is curved and so has a radius of curvature, wherein each slot has its minimum dimension substantially parallel with said radius and its maximum dimension substantially perpendicular to said radius.

The ion guide used in the present invention preferably forms a closed loop ion guiding path, and the voltage gradient and exit region preferably move around the ion guide.

According to the present invention, a DC voltage gradient is maintained along the ion guide. Preferably, the electrodes of the ion guide are axially spaced along the longitudinal axis of the ion guide and different DC voltages are applied to different ones of the axially spaced electrodes so as to form the DC voltage gradient. The DC voltage gradient region is preferably defined over a length of the ion guide extending from a first electrode at a relatively high potential to a second electrode at a relatively low potential. Progressively smaller DC potentials are preferably applied to electrodes between the first and second electrodes in a direction from the first electrode to the second electrode so as to form said voltage gradient.

A substantially uniform DC voltage gradient is preferably arranged along the DC voltage gradient region.

The ions separate out according to their ion mobility within the DC voltage gradient region.

Preferably, the DC voltage gradient is arranged over substantially the whole length of the ion guiding region at any given time, preferably except for the exit region.

The electrodes are preferably configured to confine ions in directions perpendicular to the longitudinal axis of the ion guide when said RF voltages are applied.

The electrodes are preferably arranged such that a closed loop ion guiding path is formed, which is preferably substantially circular or oval.

A drift gas is preferably arranged in said ion guide such that ions separate according to their mobility through the drift gas as they are urged along the ion guide.

Ions that exit the ion guide through the exit region are preferably transported away for further analysis and/or detection.

The present invention also provides a method of separating ions according to their ion mobility comprising: providing a circular or closed loop RF ion guide; causing ions to undergo one or more cycles around said ion guide; retaining said ions radially within said ion guide by a pseudo-potential voltage; maintaining an axial DC voltage gradient along a portion of said ion guide; and providing a rotating ion entrance/exit port which rotates around said ion guide.

The present invention also provides a method of mass spectrometry comprising separating ions according to any one or combination of the methods described above.

The present invention also provides an ion mobility separator comprising:

an ion guide having a plurality of electrodes arranged to form an ion guiding path;

a device arranged and adapted to supply RF voltages to at least some of said electrodes in order to confine ions within said ion guiding path;

a device arranged and adapted to maintain a DC voltage gradient along at least a portion of a longitudinal axis of said ion guide, such that as time progresses the portion of the ion guide along which the DC voltage gradient is maintained is moved along the ion guide; and a device arranged and adapted to provide an ion exit region which moves along said ion guide such that, in use, ions exit said ion guide at different locations at different times.

The present invention also provides an ion mobility separator comprising: a circular or closed loop RF ion guide, wherein in use ions are caused to undergo one or more cycles around said ion guide and are retained radially within said ion guide by a pseudo-potential voltage; a device arranged and adapted to maintain an axial DC voltage gradient along a portion of said ion guide; and an ion entrance/exit port which rotates, in use, around said ion guide.

The axial DC voltage gradient preferably progresses, in use, around the ion guide.

The axial DC voltage gradient preferably has a DC potential barrier towards a high potential end of the voltage gradient, wherein the DC potential barrier prevents ions from passing axially across said DC potential barrier.

The ion guide preferably comprises a plurality of electrodes each having an elongated aperture through which ions are transmitted in use.

Although the electrodes forming the ion guiding path have been described hereinabove as being apertured electrodes, it is also contemplated that other geometries of electrodes may be used to guide ions around the device. For example, the ion guide may be segmented in the longitudinal direction into a plurality of segments and each segment may comprise a plurality of electrodes arranged and configured for confining and guiding the ions. Each segment preferably comprises a top electrode, bottom electrodes and a plurality of side electrodes arranged therebetween so as to define a space between the top, bottom and side electrodes through which ions are guided. RF potentials are preferably applied to the side electrodes so as to confine ions in said space in the direction between the side electrodes. DC potentials are preferably applied to the top and/or bottom electrodes so as to confine ions in said space in the direction between the top and bottom electrodes. Less preferably, RF potentials are applied to the top and/or bottom electrodes so as to confine ions in said space in the direction between these electrodes.

Each segment may comprise a plurality of layers of side electrodes arranged between the top and bottom electrodes. Each layer preferably comprises two laterally spaced apart electrodes, which define a space therebetween for guiding ions. The bottom electrodes in each segment are also preferably two spaced apart electrodes. The bottom and side electrodes are preferably stacked in columns so as to define a space between the columns of electrodes. The top, bottom and side electrodes are preferably substantially planar and extend around the longitudinal direction of the drift cell so as to form a segment of the drift cell. The electrodes may be formed from printed circuit boards.

Ions may be radially confined within the space between the side electrodes, top electrode and bottom electrodes by applying RF potentials to the side electrodes. The same phase of an RF voltage source is preferably applied to the two side electrodes in each layer. Different phases of the RF voltage source are preferably applied to the side electrodes in adjacent layers. The side electrodes in any given layer are preferably supplied with an opposite RF voltage phase to the side electrodes in the adjacent layers. By applying RF potentials to the side electrodes, the ions are laterally confined within the space between the side electrodes. RF potentials may also be applied to the top and bottom electrodes so as to confine ions within the space in the vertical direction. However, it is preferred that only DC potentials are applied to the top and bottom electrodes so as to confine the ions in the vertical direction.

A DC voltage gradient is preferably applied to at least some of the electrodes so as to provide an axial electric field that urges ions to drift through the drift gas and around the ion guide. The DC voltage gradient may be formed by supplying different DC voltages to the electrodes of different segments of the drift cell. Different DC voltages may be supplied to the top and/or bottom electrode in different segments so as to form the voltage gradient. Additionally, or alternatively, different DC voltages may be supplied to the side electrodes of different segments so as to form the voltage gradient. For example, progressively smaller DC voltages may be applied to the electrodes of the different segments around the drift cell so as to create a voltage gradient that drives the ions along the drift length. The DC voltage gradient may then be moved around the device as described previously.

When it is desired to extract ions from the exit region of the ion guide, the potential applied to one or more of the bottom electrodes in the exit region may be altered such that ions are no longer confined within the space between the side electrodes. Rather, the altered potential causes ions to be driven radially outward between the bottom electrodes and out of the device. At first the DC potential applied to the bottom electrodes may be higher than the potential applied to the side electrodes (e.g. the average potential about which the RF voltage oscillates), such that ions remain confined within the space. At a later time, when it is desired to eject ions from the exit region, the DC potential applied to the bottom electrodes in the exit region may be dropped relative to the side electrodes. This causes ions to be radially ejected out of the device between the bottom electrodes. At a later time, the potential applied to the bottom electrodes may be restored to its original potential so as to radially confine ions within the space.

As in the previously described embodiments, the exit region from which ions are ejected moves around the ion guide along with the voltage gradient region. It will therefore be appreciated that the potentials applied to the bottom electrodes will vary as the voltage gradient moves around the ion guide such that ions are ejected from the moving exit region. The bottom electrodes around ion guide may typically all be maintained at a relatively high potential relative to their corresponding side electrodes so as to retain the ions in said space. Preferably, only the bottom electrodes in the exit region have their potentials dropped relative to their corresponding side electrodes to a relatively low potential so as to eject ions. The exit region preferably moves around the ion guide by travelling the low potential around the segments of the ion guide such that the low potential is successively applied to the bottom electrodes around the ion guide. The low potential may be travelled around the ion guide at a rate that is synchronized with the rate at which the voltage gradient travels around the ion guide, such that the exit region is collocated with an end of the voltage gradient region.

The ion mobility separator may be arranged and configured to perform any one or combination of the optional and preferred methods described herein above.

The present invention also provides a mass spectrometer comprising an ion mobility separator as described above.

According to an embodiment the mass spectrometer may further comprise:

(a) an ion source selected from the group consisting of: (i) an Electrospray ionisation ("ESI") ion source; (ii) an Atmospheric Pressure Photo Ionisation ("APPI") ion source; (ill) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation on Silicon ("DIOS") ion source; (viii) an Electron Impact ("EI") ion source; (ix) a Chemical Ionisation ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source; (xvi) a Nickel-63 radioactive ion source; (xvii) an Atmospheric Pressure Matrix Assisted Laser Desorption Ionisation ion source; (xviii) a Thermospray ion source; (xix) an Atmospheric Sampling Glow Discharge Ionisation ("ASGDI") ion source; (xx) a Glow Discharge ("GD") ion source; and (xxi) an Impactor ion source; and/or (b) one or more continuous or pulsed ion sources; and/or (c) one or more additional ion guides; and/or (d) one or more additional ion mobility separation devices and/or one or more Field Asymmetric Ion Mobility Spectrometer devices; and/or (e) one or more ion traps or one or more ion trapping regions; and/or (f) one or more collision, fragmentation or reaction cells selected from the group consisting of: (i) a Collisional Induced Dissociation ("CID") fragmentation device; (ii) a Surface Induced Dissociation ("SID") fragmentation device;

(iii) an Electron Transfer Dissociation ("ETD") fragmentation device; (iv) an Electron Capture Dissociation ("ECD") fragmentation device; (v) an Electron Collision or Impact Dissociation fragmentation device; (vi) a Photo Induced Dissociation ("PID") fragmentation device; (vii) a Laser Induced Dissociation fragmentation device; (viii) an infrared radiation induced dissociation device; (ix) an ultraviolet radiation induced dissociation device; (x) a nozzle-skimmer interface fragmentation device; (xi) an in-source fragmentation device; (xii) an in-source Collision Induced Dissociation fragmentation device; (xiii) a thermal or temperature source fragmentation device; (xiv) an electric field induced fragmentation device; (xv) a magnetic field induced fragmentation device; (xvi) an enzyme digestion or enzyme degradation fragmentation device; (xvii) an ion-ion reaction fragmentation device; (xviii) an ion-molecule reaction fragmentation device; (xix) an ion-atom reaction fragmentation device; (xx) an ion-metastable ion reaction fragmentation device; (xxi) an ion-metastable molecule reaction fragmentation device; (xxii) an ion-metastable atom reaction fragmentation device; (xxiii) an ion-ion reaction device for reacting ions to form adduct or product ions; (xxiv) an ion-molecule reaction device for reacting ions to form adduct or product ions; (xxv) an ion-atom reaction device for reacting ions to form adduct or product ions; (xxvi) an ion-metastable ion reaction device for reacting ions to form adduct or product ions; (xxvii) an ion-metastable molecule reaction device for reacting ions to form adduct or product ions; (xxviii) an ion-metastable atom reaction device for reacting ions to form adduct or product ions; and (xxix) an Electron Ionisation Dissociation ("EID") fragmentation device; and/or (g) a mass analyser selected from the group consisting of: (i) a quadrupole mass analyser; (ii) a 2D or linear quadrupole mass analyser; (iii) a Paul or 3D quadrupole mass analyser; (iv) a Penning trap mass analyser; (v) an ion trap mass analyser; (vi) a magnetic sector mass analyser; (vii) Ion Cyclotron Resonance ("ICR") mass analyser; (viii) a Fourier Transform Ion Cyclotron Resonance ("FTICR") mass analyser; (ix) an electrostatic or orbitrap mass analyser, (x) a Fourier Transform electrostatic or orbitrap mass analyser; (xi) a Fourier Transform mass analyser; (xii) a Time of Flight mass analyser; (xiii) an orthogonal acceleration Time of Flight mass analyser; and (xiv) a linear acceleration Time of Flight mass analyser; and/or (h) one or more energy analysers or electrostatic energy analysers; and/or (i) one or more ion detectors; and/or (j) one or more mass filters selected from the group consisting of: (i) a quadrupole mass filter; (ii) a 2D or linear quadrupole ion trap; (iii) a Paul or 3D quadrupole ion trap; (iv) a Penning ion trap; (v) an ion trap; (vi) a magnetic sector mass filter, (vii) a Time of Flight mass filter, and (viii) a Wein filter; and/or (k) a device or ion gate for pulsing ions; and/or (l) a device for converting a substantially continuous ion beam into a pulsed ion beam.

The mass spectrometer may further comprise either:

(i) a C-trap and an Orbitrap™ mass analyser comprising an outer barrel-like electrode and a coaxial inner spindle-like electrode, wherein in a first mode of operation ions are transmitted to the C-trap and are then injected into the Orbitrap™ mass analyser and wherein in a second mode of operation ions are transmitted to the C-trap and then to a collision cell or Electron Transfer Dissociation device wherein at least some ions are fragmented into fragment ions, and wherein the fragment ions are then transmitted to the C-trap before being injected into the Orbitrap™ mass analyser; and/or (ii) a stacked ring ion guide comprising a plurality of electrodes each having an aperture through which ions are transmitted in use and wherein the spacing of the electrodes increases along the length of the ion path, and wherein the apertures in the electrodes in an upstream section of the ion guide have a first diameter and wherein the apertures in the electrodes in a downstream section of the ion guide have a second diameter which is smaller than the first diameter, and wherein opposite phases of an AC or RF voltage are applied, in use, to successive electrodes.

According to an embodiment the mass spectrometer further comprises a device arranged and adapted to supply an AC or RF voltage to the electrodes. The AC or RF voltage preferably has an amplitude selected from the group consisting of: (i) <50 V peak to peak; (ii) 50-100 V peak to peak; (iii) 100-150 V peak to peak; (iv) 150-200 V peak to peak; (v) 200-250 V peak to peak; (vi) 250-300 V peak to peak; (vii) 300-350 V peak to peak; (viii) 350-400 V peak to peak; (ix) 400-450 V peak to peak; (x) 450-500 V peak to peak; and (xi) >500 V peak to peak.

The AC or RF voltage preferably has a frequency selected from the group consisting of: (i) <100 kHz; (ii) 100-200 kHz; (iii) 200-300 kHz; (iv) 300-400 kHz; (v) 400-500 kHz; (vi) 0.5-1.0 MHz; (vii) 1.0-1.5 MHz; (viii) 1.5-2.0 MHz; (ix) 2.0-2.5 MHz; (x) 2.5-3.0 MHz; (xi) 3.0-3.5 MHz; (xii) 3.5-4.0 MHz; (xiii) 4.0-4.5 MHz; (xiv) 4.5-5.0 MHz; (xv) 5.0-5.5 MHz; (xvi) 5.5-6.0 MHz; (xvii) 6.0-6.5 MHz; (xviii) 6.5-7.0 MHz; (xix) 7.0-7.5 MHz; (xx) 7.5-8.0 MHz; (xxi) 8.0-8.5 MHz; (xxii) 8.5-9.0 MHz; (xxiii) 9.0-9.5 MHz; (xxiv) 9.5-10.0 MHz; and (xxv) >10.0 MHz.

The preferred embodiment relates to a multi-pass ion mobility separator (IMS) device having a voltage gradient and exit region that move along the device. The device enables a larger range of mobilities to be retained and then analysed with high mobility resolution. In the preferred embodiment the IMS device guides ions around a closed loop. There is a trade off between mobility resolution of such a device and the range of mobilities that can be accommodated. The higher the resolution of the device (i.e. the higher the number of times that ions are cycled around the device), the lower the range of mobilities is that can be retained on the voltage gradient. By employing a moving exit region and a potential barrier on the voltage gradient, the preferred embodiment enables both high mobility resolution and full mobility range studies to be achieved.

The preferred device comprises electrodes forming a closed loop ion guide and RF voltages are applied to the electrodes so as to radially confine ions within the electrodes such that the ions can be guided around the ion guide. A DC voltage gradient is superimposed on the confining RF voltages so as to drive the ions around the closed loop, enabling the ions to separate according to their mobilities.

The DC voltage gradient is preferably progressed around the closed loop, following the motion of the mobility separating ions. With time, ion species reach the end of the voltage gradient in a mobility dependent manner. At the point in time that the ions reach the end of the voltage gradient the ions are preferably extracted from the ion guide and transported away for further analysis or detection. As such, the ion exit region preferably tracks the end point of the voltage gradient as it progresses around the closed loop. A potential barrier may be employed at the high voltage end or the low voltage end of the potential gradient to prevent ions leaving the separation region (i.e. voltage gradient region) at these points. The rate at which the potential gradient cycles around the device may be decreased or increased with time so as to cause ions to separate along the gradient and ultimately exit the device by passing over the high or low potential end of the voltage gradient, i.e. the opposite end to the potential barrier. As these ions leave the voltage gradient they are preferably extracted and transported away for further analysis. By using a potential barrier, changing the rate of cycling of the voltage gradient around the ion guide and the moving exit region around the ion guide, a wide range of mobilities can be analysed at high resolution.

BRIEF DESCRIPTION OF THE DRAWINGS

Various embodiments of the present invention will now be described, by way of example only, and with reference to the accompanying drawings in which:

FIG. 3A shows a plan view of the arrangement of electrodes in an embodiment of the present invention, and FIGS. 3B and 3C show schematics of the embodiment illustrating the location of the ion exit region at different times;

DETAILED DESCRIPTION OF PREFERRED EMBODIMENTS

The resolving power R of an ion mobility spectrometer (IMS) that uses a uniform electric field is given by the expression:

$$R = \frac{t}{t_{FWHM}} = \left(\frac{LEze}{16kT\ln 2}\right)^{0.5} = \left(\frac{Vze}{16kT\ln 2}\right)^{0.5}$$

wherein t is the ion drift time through the drift region of the device; $t_{FWHM}$ is the peak width at half height of the signal; L is the length of the drift region; E the electric field strength; z is the number of charges on the ion being analysed; e is the unit electronic charge; V is the potential difference across the drift region of the device (E=V/L); k is Boltzmann's constant; and T is the temperature of the drift gas in the drift region.

It is apparent from the above expression that the potential difference V across the drift region of the IMS device can be increased in order to increase the resolution of the device. However, increasing the potential difference across a fixed length of drift region will ultimately result in electrical breakdown in the drift gas. In order to further increase the resolution of the device it is therefore conventionally considered necessary to increase the length of the drift region L. However, if the length of the drift region L is increased then a greater potential difference must be applied across the drift region in order to maintain the same electric field strength over the longer drift region.

Figure 1:
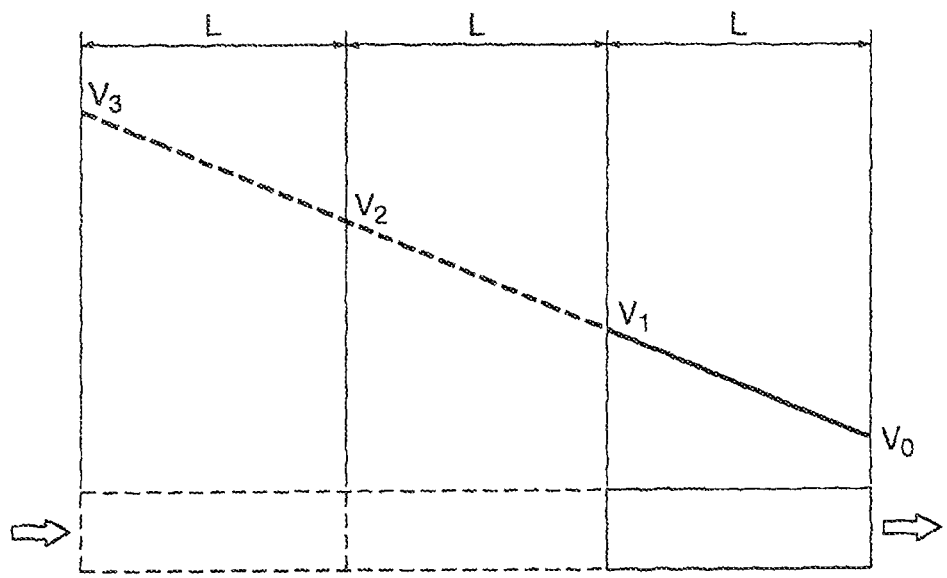
FIG. 1 shows an example of the voltages that must be applied to drift regions of different lengths in order to maintain the same electric field strength along the different lengths of drift region.

FIG. 1 shows an example of the voltages that must be applied to drift regions of different lengths in order to maintain the same electric field strength along the different lengths of drift region. If the drift region only has a length L then a voltage $V_0$ may be applied at the exit of the drift region and a higher voltage $V_1$ may be applied at the entrance to the drift region in order to provide an electric field across the drift region. The electric field drives ions through a drift gas that is present in the drift region, such that the ions separate according to their mobility through the drift gas as they pass through the drift region. If the length of the drift region is doubled to 2L and the same voltage $V_0$ is applied at the exit of the drift region, then the voltage applied at the entrance of the drift region must be increased to $V_2$ in order to maintain the same electric field strength along the drift region of length 2L as was present along the drift region of length L. Similarly, if the length of the drift region is increased to 3L and the same voltage $V_0$ is applied at the exit of the drift region, then the voltage applied at the entrance of the drift region must be increased to $V_3$ in order to maintain the same electric field strength along the drift region of length 3L as was present along the drift region of length L. This conventional approach ultimately leads to an extremely long drift region and hence a large IMS device. Also, this conventional approach requires the use of a relatively large potential difference in order to achieve the desired electric field strength along the relatively long drift region. The use of high absolute voltages to achieve this can lead to electrical breakdown to the surroundings, which can be hazardous.

Figure 2:
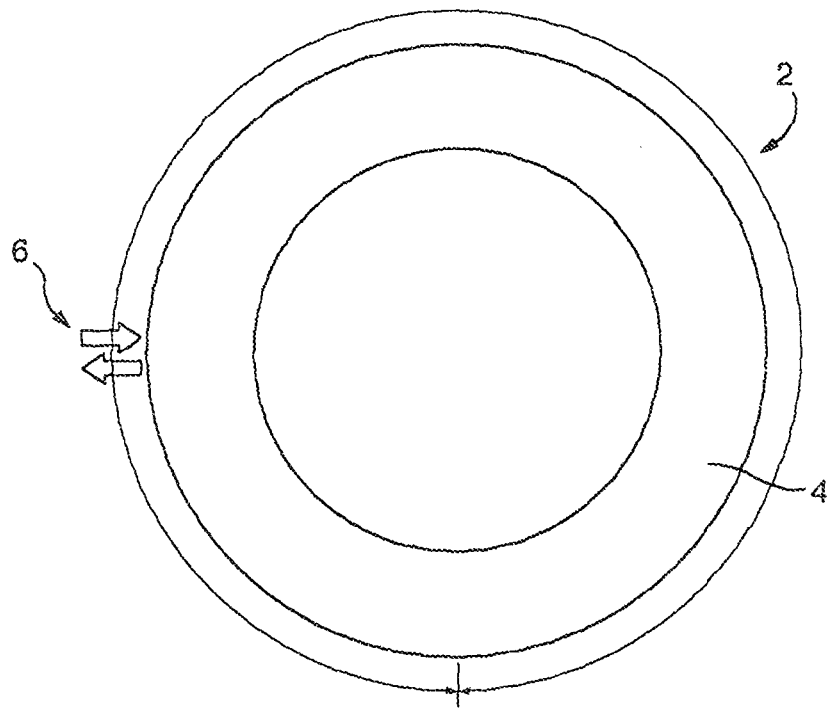
FIG. 2 shows an ion mobility separator having a circular drift length.

FIG. 2. shows an IMS device 2 designed to overcome the above-mentioned problem of having to provide a physically large drift region. The IMS device 2 comprises a drift cell 4 having electrodes for guiding ions along a drift length that is arranged as a continuous circular geometry. Ions may be introduced into the device at an entry region 6. After the ions have entered the device 2 they are caused to move around the drift length of the device by applying voltages to the electrodes of the device. More specifically, a voltage gradient is arranged along the drift length so that the ions are urged along the drift length. A drift gas is present in the drift length and causes the ions to separate out according to their ion mobilities through the drift gas as they pass along the drift length. The voltage gradient is conveyed around the drift cell 4 as the ions move around the drift cell 4, in an attempt to maintain the ions within the voltage gradient region so that the ions continue to separate as they move around the drift cell 4. As the device is circular, the ions and voltage gradient may be cycled around the drift cell 4 as many times as is necessary to provide the required overall length of drift for the ions and thus the desired ion mobility resolution. After this, the ions are extracted from the device 2 at exit region 6, which is at the same location as the entry region 6.

In such a device, the range of ion mobilities that can be analysed in a given experiment is determined by the physical length of the voltage gradient region and the temporal length of the mobility separation experiment. For example, if the voltage gradient progresses around the device 2 at the same rate that the lowest mobility ion species would move down the voltage gradient if the gradient was static, then the lowest ion mobility species will remain at a constant position relative to the voltage gradient as the voltage gradient cycles around the device 2. In contrast, the highest mobility ion species will travel down the voltage gradient and will eventually reach the low potential end of the voltage gradient. Once these ions have reached the low potential end no further mobility separation will occur for this species. If these ions are not at the exit region 6 of the device 2 at the time that they reach the low potential end of the voltage gradient then there is a period during which the voltage gradient is required to be cycled further around the device 2 until the ions reach the exit region 6. During this period, ions of lower mobility than the highest mobility ions may continue to move down the voltage gradient and may also reach the low potential end of the voltage gradient and re-merge with the highest mobility ions. This results in a loss of mobility separation within the device 2. This problem may be exacerbated if the device is operated in a mode in which the ions are cycled around the device 2 multiple times.

In the above-described arrangement it is possible to provide relatively high resolution on a relatively small range of ion mobilities by tuning the rate at which the voltage gradient is cycled around the drift cell 4 to the ion mobility range of interest. Ion species having mobilities below the range of interest will travel towards the high potential end of the voltage gradient as the gradient cycles around the drift cell and these ions will eventually leave the voltage gradient region from the high potential end. Ion species having mobilities above the range of interest will travel towards the low potential end of the voltage gradient as it cycles around the drift cell and will eventually leave the voltage gradient region from the low potential end and re-merge with other ions. The ions of interest will separate out in a desired manner as they drift towards the low potential end of the voltage gradient. This technique is therefore limited in the range of ion mobilities that can be analysed at a reasonable resolution.

FIGS. 3A to 3C show a preferred embodiment of a drift cell according to the present invention. FIG. 3A shows a plan view of the basic electrode structure of the drift cell 4 and FIGS. 3B and 3C show schematics of the drift cell in operation at two different points in time. Referring to FIG. 3A, the drift cell 4 may be formed from a plurality of planar, apertured electrodes 8 that are arranged in a circle and such that each electrode 8 lies in a plane that extends radially outward from the centre of the drift cell 4. Voltages are applied to the electrodes 8 so as guide ions through the apertures 10 in the successive electrodes 8 and hence around the drift cell 4. More specifically, RF voltages may be applied to the electrodes 8 so as to radially confine the ions and provide an ion guiding path through the apertures 10 of the electrodes 8. Alternate electrodes 8 in the drift cell 4 are preferably applied with different phases of an RF voltage source. Alternate electrodes 8 in the drift cell 4 are preferably applied with opposite phases of the RF voltage source, i.e. when a given electrode 8 is at an RF phase of 0 degrees the adjacent electrodes 8 are preferably at 180 degrees. A DC voltage gradient is applied to the electrodes 8 and is superimposed on the RF voltages so as to provide an axial electric field that urges ions to drift through the drift gas and around the drift cell 4.

In the example shown in FIG. 3A, an electrode is maintained at a relatively high voltage $V_1$ and an adjacent electrode is maintained at a relatively low voltage $V_0$. This provides a force on the ions away from the electrode at high voltage $V_1$ and to pass around the drift cell 4 in a clockwise manner towards the electrode at low voltage $V_0$. At least some of the electrodes 8 that are arranged between the two electrodes held at $V_1$ and $V_0$ also preferably have DC potentials applied to them so as to maintain a voltage gradient that decreases between said two electrodes. For example, progressively smaller DC voltages may be applied to the electrodes around the drift cell 4 so as to create a voltage gradient that drives the ions along the drift length. The DC voltage gradient may be generated using a resistor chain coupled to the electrodes forming the drift cell 4 and across which a potential difference is applied. The voltage gradient drives ions through the drift region and causes ions to separate according to their mobility. It will be appreciated that although a decreasing voltage gradient has been described for urging positive ions around the device, an increasing voltage gradient may be used to urge negative ions around the device.

In the above example, the DC voltage gradient applied to the device is arranged along substantially the whole length of the drift region. Alternatively, a DC potential difference may be arranged along only a portion of the length of the drift region.

As described above. DC voltages are applied to the electrodes forming the drift cell 4 so as to form a DC voltage gradient and axial electric field region along the drift cell 4. The electrodes 8 to which these DC voltages are applied is then changed with time so that the length over which the DC voltage gradient is maintained is moved around the drift cell 4, preferably in a manner such that as the ions pass around the drift cell at least some of them always remain within the electric field region until they exit the device. This ensures that the ions experience a uniform electric field strength as they pass around the drift cell 4. The DC voltage gradient can be cycled around the drift cell 4 multiple times as the ions cycle around the drift cell 4. Thus by providing a DC voltage gradient that cycles around the drift cell 4, ions can be made to travel along a relatively long drift path without having to provide a physically large drift region. The axial DC voltage gradient may be progressively stepped around the device in steps of single electrodes 8 or in steps of multiple electrodes 8. However, it is observed that increasing the number of electrodes 8 by which the voltage gradient is stepped around the device effectively reduces the range of ion mobilities which can be retained in the axial electric field region.

Ions separate out as they pass through the drift region and ions will move towards the low potential end of the voltage gradient in order of high to low ion mobility. When ions reach the low potential end of the voltage gradient it is desired to extract them from the drift cell so that these ions do not remerge with other ions. The ions are therefore preferably extracted at the point in time when they reach the low potential end of the voltage gradient. As the voltage gradient is cycled around the drift cell 4, and as high mobility ions reach the low potential end of the voltage gradient at a different time to lower mobility ions, the exit region 6 of the drift cell 4 is also cycled around the drift cell 4.

FIG. 3B shows the drift cell 4 at a first point in time when relatively high mobility ions have reached the low potential end 12 of the voltage gradient and are exiting the drift cell 4 at the exit region 6. The voltage gradient is represented by the line 14 around the drift cell 4 and extends from a high potential end 16 to a low potential end 12. FIG. 3C shows the drift cell 4 at a second, later point in time when relatively low mobility ions have reached the low potential end 12 of the voltage gradient 14 and are exiting the drift cell 4 at the exit region 6. As can be seen from FIGS. 3B and 3C, the exit region 6 has moved around the drift cell 4 with time such that any given ion can be extracted at the time that it reaches the low potential end 12 of the voltage gradient 14. Ions that are extracted may be transported away for further analysis and/or detection. As such, ions which reach the low potential end 12 of the gradient 14 do not re-merge with other ions and their mobility separation can be preserved and recorded.

It is necessary to select the speed at which the voltage gradient 14 is moved around the drift cell 4 depending upon the ion mobilities that are desired to be separated and extracted, and depending on the resolution that is desired. For example, if the voltage gradient 14 is moved around the drift cell 4 at a relatively high speed then ions of relatively low mobility may exit the voltage gradient region 14 at the high potential end 16. In order to retain the relatively low mobility ions within the voltage gradient region 14 and to cause them to separate in the voltage gradient region 14, it is necessary to set the speed at which the voltage gradient region 14 moves around the drift cell 4 to be lower than the speed at which the low mobility ions travel around the drift cell 4. On the other hand, if the voltage gradient 14 is moved around the drift cell 4 at a relatively low speed then ions of relatively high mobility may exit the voltage gradient region 14 at the low potential end 12 and exit the drift cell 4 only having travelled a relatively short distance through the drift cell 4. This may result in relatively low resolution for these ions. A mode of operation for improving the analysis of ions having a relatively wide range of mobilities will be described in relation to FIGS. 4A to 4C.

Figure 4A:
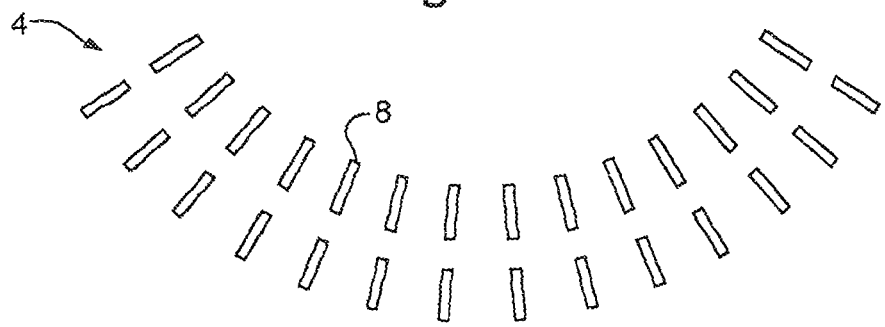
FIG. 4A shows a plan view of a portion of the embodiment of FIGS. 3A to 3C, and FIGS. 4B and 4C show DC voltage potential profiles along this portion at different times during the ions separation process.
Figure 4B:
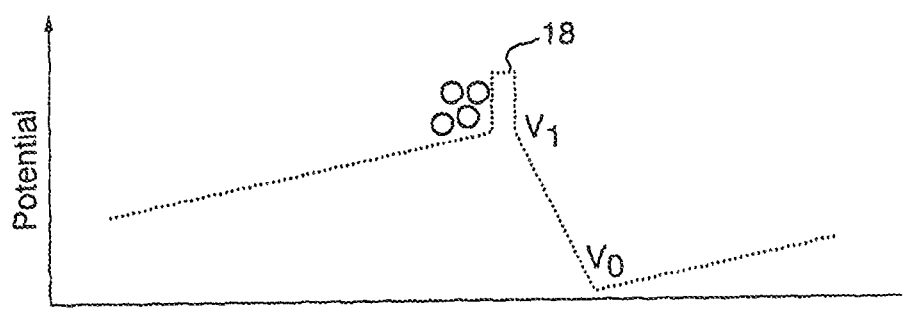
Figure 4C:
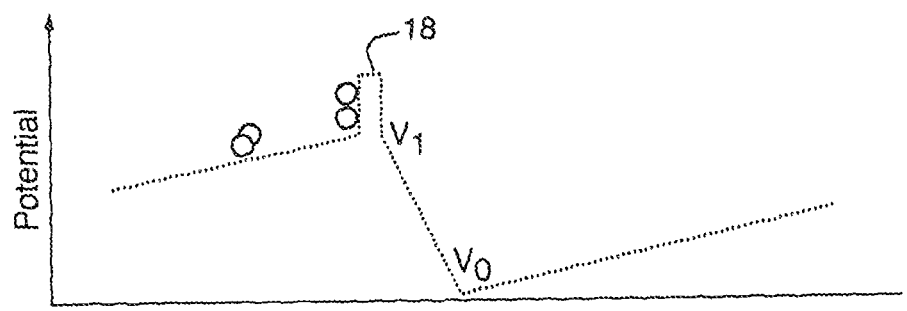

FIG. 4A shows a portion of the drift cell 4 of FIGS. 3A to 3C. FIGS. 4B and 4C show DC potential profiles along this portion of the drift cell 4 at different times during the ion separation process. As described previously, DC voltages are applied to the electrodes 8 so as to form a DC voltage gradient around the drift cell 4. This gradient can be seen in FIG. 4B and extends clockwise around the drift cell 4 (as viewed from above) from a high voltage end $V_1$ to a low voltage end $V_0$. A DC potential barrier 18 is also imposed at the high potential end $V_1$ of the voltage gradient. This potential barrier 18 is configured such that it prevents any ions from exiting the voltage gradient region from the high potential end $V_1$ of the voltage gradient region. As such, even if the voltage gradient region is moved around the drift cell 4 at a rate that is faster than the rate at which ions would drift down the voltage gradient if the gradient was static, these ions are unable to leave the voltage gradient region at the high potential end $V_1$. FIG. 4B shows the position of the ions and the voltage gradient at a first time when the voltage gradient is moving clockwise around the drift cell 4 at a relatively high speed. Low mobility ions are represented by dark circles and high mobility ions are represented by light circles. At the time depicted in FIG. 4B, the voltage gradient is moving too fast for either the high or low mobility ions to travel down the voltage gradient. Rather, the Ions are forced around the drift cell 4 by the potential barrier 18 located behind them.

FIG. 4C depicts the location of the ions and voltage gradient at a later time when the speed at which the voltage gradient is moving around the drift cell 4 has been reduced. The speed of the voltage gradient has been reduced to an extent such that the drift speed of the high mobility ions around the drift cell 4 (caused by the voltage gradient) is greater than the speed at which the voltage gradient is moving around the drift cell 4. As such, the high mobility ions begin moving towards the low potential end $V_0$ of the voltage gradient. On the other hand, the speed of the voltage gradient remains higher than the speed at which the low mobility ions would drift along the voltage gradient if the voltage gradient was static. As such, the low mobility ions remain adjacent to the potential barrier 18 and are forced around the drift cell 4 by the potential barrier 18. By reducing the speed at which the voltage gradient moves around the drift cell 4 the high mobility ions can therefore be separated from other ions and exit from the drift cell 4 at the time that they reach the low potential end $V_0$ of the voltage gradient. The speed of the voltage gradient can remain sufficiently high such that the high mobility ions travel a relatively long distance around the drift region, e.g. many cycles around the drift cell 4, within the voltage gradient region before the ions exit the drift cell 4, so as to achieve high resolution. Lower ion mobility ions are not lost from the fast moving voltage gradient region because the potential barrier 18 prevents them from exiting the high potential end $V_1$ of the voltage gradient region.

At a later time the speed at which the voltage gradient is moved around the drift cell 4 may be reduced still further, such that the lower mobility ions start to drift down the voltage gradient and away from the potential barrier 18. These lower mobility ions can then pass to the low potential end $V_0$ of the voltage gradient and exit the drift cell 4 at the time that they reach the low potential end $V_0$. At a later time still, the speed at which the voltage gradient is moved around the drift cell 4 may be reduced even further, such that even lower mobility ions start to drift down the voltage gradient and away from the potential barrier 18. Again, these ions can then pass to the low potential end $V_0$ of the voltage gradient and exit the drift cell 4 at the time that they reach the end $V_0$. In this manner, all of the ion species covering a range of mobilities can be separated with high resolution. It will be noted that the resolution is dependent on mobility.

It is contemplated that the speed at which the voltage gradient is moved around the drift cell 4 may be decelerated in a linear or non-linear manner. For example, the voltage gradient may be continuously and progressively decelerated or be stepped down in velocity in a discontinuous manner.

In an alternative mode of operation to that described above, the potential barrier 18 may be arranged at the low potential end $V_0$ of the voltage gradient rather than the high potential end $V_1$. The voltage gradient may initially be static or may be moved around the drift cell 4 at a relatively slow rate. As such, all ions are urged down the voltage gradient towards the potential barrier 18 and are trapped adjacent the potential barrier 18. In order to enact separation, the speed of the voltage gradient is increased (in the direction of high to low potential of the voltage gradient) to an extent such that the drift speed of the low mobility ions around the drift cell 4 is lower than the speed at which the voltage gradient is moving around the drift cell 4. As such, the low mobility ions begin moving towards the high potential end $V_1$ of the voltage gradient. On the other hand, the speed of the voltage gradient remains lower than the speed at which higher mobility ions would drift along the voltage gradient if the voltage gradient was static. As such, the higher mobility ions remain forced against the potential barrier 18 by the voltage gradient as the voltage gradient region moves around the drift cell 4. By increasing the speed at which the voltage gradient moves around the drift cell 4 the low mobility ions can therefore be separated from other ions and exit from the drift cell 4 at the time that they reach the high potential end $V_1$ of the voltage gradient. The speed of the voltage gradient can remain sufficiently low such that the low mobility ions travel a relatively long distance around the drift region, e.g. many cycles around the drift cell, within the voltage gradient region before the ions reach the high potential end $V_1$ and exit the drift cell 4, so as to achieve high resolution. Higher mobility ions are not lost from the slow moving voltage gradient region because the potential barrier 18 prevents them from exiting the low potential end $V_0$ of the voltage gradient region.

At a later time the speed at which the voltage gradient is moved around the drift cell 4 may be increased further, such that higher mobility ions start to drift up the voltage gradient and away from the potential barrier 18. These higher mobility ions can then pass to the high potential end $V_1$ of the voltage gradient and exit the drift cell 4 at the time that they reach the high potential end $V_1$. At a later time still, the speed at which the voltage gradient is moved around the drift cell 4 may be increased even further, such that even higher mobility ions start to drift up the voltage gradient and away from the potential barrier 18. Again, these ions can then pass to the high potential end $V_1$ of the voltage gradient and exit the drift cell 4 at the time that they reach the high potential end $V_1$. In this manner, all of the ion species covering a range of mobilities can be separated with high resolution. Again, the resolution is dependent on mobility.

It is contemplated that the speed at which the voltage gradient is moved around the drift cell 4 may be accelerated in a linear or non-linear manner. For example, the voltage gradient may be continuously and progressively accelerated or may be stepped up in velocity in a discontinuous manner.

Figure 5A:
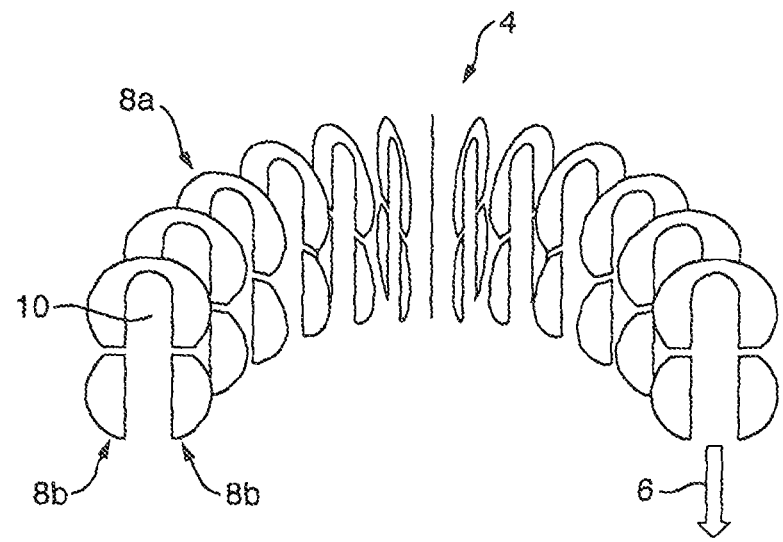
FIG. 5A shows a schematic view of a portion of the embodiment of FIGS. 3A to 3C and illustrates the apertured electrodes and gate electrodes of the ion guide.
Figure 5B:
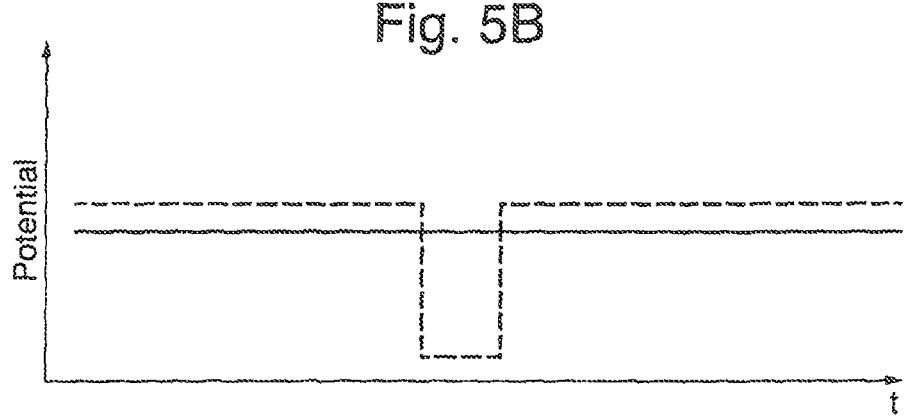
FIG. 5B shows the potentials applied to an apertured electrode and its corresponding gate electrodes as a function of time.

FIGS. 5A and 5B illustrate the manner by which ions may be ejected from the drift cell 4 when they reach an end of the voltage gradient. FIG. 5A shows a schematic of the electrodes forming a sector of the drift cell 4. The drift cell 4 is formed from a plurality of planar, apertured electrodes 8a and planar gate electrodes 8b that are arranged in a circle and such that each electrode 8a,8b lies in a plane that extends radially outward from the centre of the drift cell 4. In this example the apertured electrodes 8a have slotted apertures 10, wherein a slot is formed into an edge of each electrode 8a. Voltages are applied to the electrodes 8a so as guide ions through the apertures 10 in the successive electrodes 8a and hence around the drift cell 4. More specifically, RF voltages may be applied to the electrodes 8a so as to radially confine the ions and provide an ion guiding path through the apertures 10 of the electrodes 8a. Alternate electrodes 8a in the drift cell 4 are preferably applied with different phases of an RF voltage source. Alternate electrodes 8a in the drift cell 4 are preferably applied with opposite phases of the RF voltage source, i.e. when a given electrode 8a is at an RF phase of 0 degrees the adjacent electrodes 8a are preferably at 180 degrees.

The configuration of the apertured electrodes 8a does not confine ions at the radial edge that the slot is formed into. Rather, two gate electrodes 8b are arranged adjacent to the slotted opening in each apertured electrode 8a. The gate electrodes 8b are generally maintained at a potential such that the ions within the apertured electrodes 8a are not able to pass radially outwards through the open side of the slot 10. For example, the gate electrodes 8b are held at a slightly higher potential than their corresponding apertured electrode 8a.

A DC voltage gradient is applied to at least some of the apertured electrodes 8a and is preferably superimposed on the RF voltages so as to provide an axial electric field that urges ions to drift through the drift gas and around the drift cell 4.

When it is desired to extract ions from an exit region 6 of the drift cell 4, the potential applied to one or more of the gate electrodes 8b in the exit region 6 is altered such that ions are no longer confined within the apertured electrodes 8a of the exit region 6. Rather, the altered potential causes ions to be driven radially outward through the open side of the slot 10 in the apertured electrode 8a, between the gate electrodes 8b and out of the device 4. FIG. 5B shows an example of the DC potentials applied to the apertured electrodes 8a and gate electrodes 8b as a function of time. The DC potential applied to the apertured electrodes 8a is shown as a solid line. This may be the average potential about which the RF radial confinement voltage oscillates. The DC potential applied to the gate electrodes 8b is shown as the broken line. At first the DC potential applied to the gate electrodes 8b is higher than the DC potential applied to the apertured electrodes 8a, such that ions remain confined within the apertured electrodes 8a. At a later time, when it is desired to eject ions from the exit region 6 of the drift cell 4, the potential applied to the gate electrodes 8b in the exit region 6 is dropped relative to their corresponding apertured electrode 8a. This causes ions to be radially ejected out of the open side of the slot 10 in the apertured electrode 8a, between the gate electrodes 8b and out of the drift cell 4. At a later time, the potential applied to the gate electrodes 8b is restored to its original potential so as to radially confine ions within the apertured electrodes 8a.

As described earlier, particularly in relation to FIGS. 3B and 3C, the exit region 6 from which ions are ejected from the drift cell 4 moves around the drift cell 4 along with the voltage gradient region 14. In particular, the exit region 6 preferably remains located at the region of the drift cell 4 at which the low potential end 12 of the voltage gradient is located. In another of the methods described above, the exit region 6 preferably remains located at the region of the drift cell 4 at which the high potential end 16 of the voltage gradient is located. It will therefore be appreciated that the potentials applied to the gate electrodes 8b will vary as the voltage gradient 14 moves around the drift cell 4 such that ions are ejected from the moving exit region 6. The gate electrodes 8b around the drift cell 4 are typically all maintained at a relatively high potential relative to their corresponding apertured electrodes 8a so as to retain the ions in the apertured electrodes 8a. Only the gate electrodes 8b in the exit region 6 have their potentials dropped relative to their corresponding apertured electrode(s) 8a to a relatively low potential so as to eject ions. The exit region 6 moves around the drift cell 4 by travelling the low potential around the drift cell 4 such that the low potential is successively applied to the gate electrodes 8b around the drift cell 4. The low potential is travelled around the drift cell 4 at a rate that is synchronized with the rate at which the voltage gradient travels around the drift cell 4, such that the exit region 6 is collocated with an end of the voltage gradient region 14.

Although the electrodes forming the drift cell have been described hereinabove as being apertured electrodes, it is also contemplated that other geometries of electrodes may be used to guide ions around the drift cell.

Figure 6A:
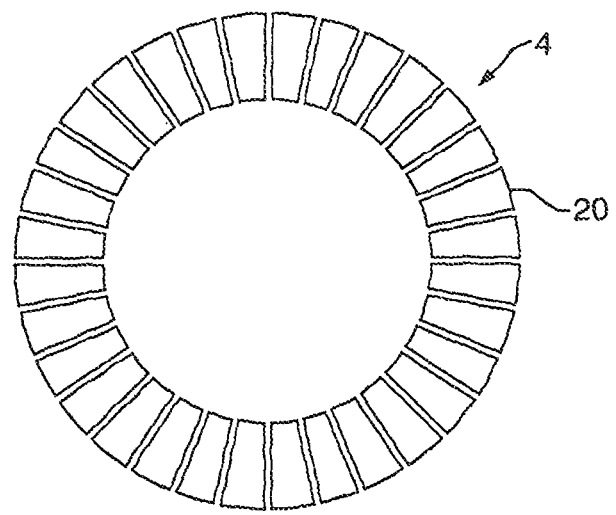
FIG. 6A shows a plan view of the arrangement of the electrodes in an embodiment of the present invention.

FIG. 6A shows a preferred embodiment of the arrangement of the electrodes in the drift cell 4 from a plan view. Rather than the drift cell 4 being formed from a plurality of apertured electrodes 8 that are arranged in a circle, the drift cell is divided into segments 20, wherein each segment 20 comprises a plurality of layers of electrodes, as shown in FIG. 6B.

Figure 6B:
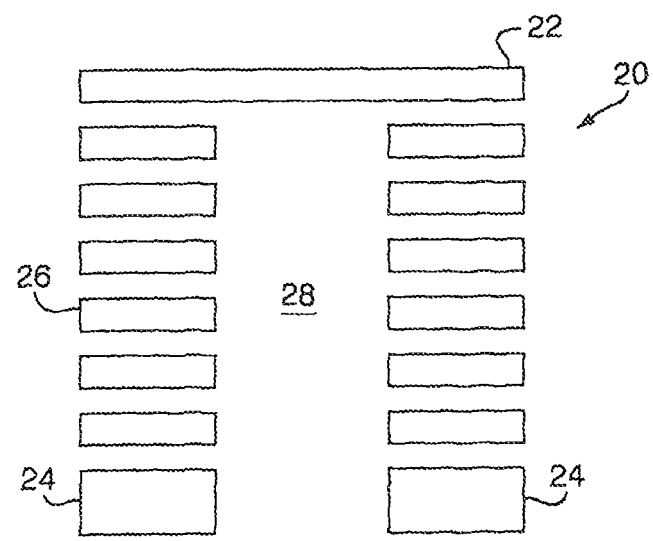
FIG. 6B shows a schematic of a cross section through the drift cell.

FIG. 6B shows a cross-section through one of the segments 20 in FIG. 6A. Each segment 20 is formed from a top electrode 22, bottom electrodes 24 and a plurality of layers of electrodes 26 arranged therebetween. Each layer comprises two laterally spaced apart electrodes 26 arranged such that these electrodes 26 form side electrodes. The bottom electrodes 24 are also laterally spaced apart. The side electrodes 26 and bottom electrodes 24 are stacked in columns so as to define a space 28 between the columns of side electrodes 26, and between the top and bottom electrodes 22,24. The top, bottom and side electrodes 22,24,26 are substantially planar and extend around the longitudinal direction of the drift cell 4 so as to form a segment 20 of the drift cell 4, as shown in FIG. 6A. The planar electrodes 22,24,26 extend in the plane that ions travel in, in use.

Ions are radially confined within the space 28 between the side electrodes 26, top electrode 22 and bottom electrodes 24. In order to achieve this confinement, RF potentials are applied to the side electrodes 26. The same phase of an RF voltage source is preferably applied to the two side electrodes 26 in each layer. Different phases of the RF voltage source are preferably applied to the side electrodes 26 in adjacent layers. The side electrodes 26 in any given layer are preferably supplied with an opposite RF voltage phase to the side electrodes 26 in the adjacent layers. By applying RF potentials to the side electrodes 26, the ions are laterally confined within the space 28 between the side electrodes 26. RF potentials may also be applied to the top and bottom electrodes 22,24 so as to confine ions within the space 28 in the vertical direction. However, it is preferred that only DC potentials are applied to the top and bottom electrodes 22,24 so as to confine the ions in the vertical direction.

Although the drift cell 4 has a different electrode configuration to the earlier described embodiments having apertured electrodes 8, the operation of the drift cell 4 is substantially the same. A DC voltage gradient is applied to at least some of the electrodes so as to provide an axial electric field that urges ions to drift through the drift gas and around the drift cell 4. The DC voltage gradient may be formed by supplying different DC voltages to the electrodes of different segments 20 of the drift cell 4. Different DC voltages may be supplied to the top 22 and/or bottom 24 electrodes in different segments 20 so as to form the voltage gradient. Additionally, or alternatively, different DC voltages may be supplied to the side electrodes 26 of different segments 20 so as to form the voltage gradient. For example, progressively smaller DC voltages may be applied to the electrodes of the different segments 20 around the drift cell 4 so as to create a voltage gradient that drives the ions along the drift length. As described in relation to the earlier embodiments, the DC voltage gradient may then be moved around the device with the ions.

When it is desired to extract ions from an exit region 6 of the drift cell 4, the potential applied to one or more of the bottom electrodes 24 (i.e. gate electrodes) in the exit region 6 is altered such that ions are no longer confined within the space 28 between the side electrodes 26. Rather, the altered potential causes ions to be driven radially outward between the bottom electrodes 24 and out of the device 4. At first the DC potential applied to the bottom electrodes 24 is higher than the DC potential applied to the side electrodes 26, such that ions remain confined within the space 28. At a later time, when it is desired to eject ions from the exit region 6 of the drift cell 4, the DC potential applied to the bottom electrodes 24 in the exit region 6 is dropped relative to the side electrodes 26. This causes ions to be radially ejected out of the device between the bottom electrodes 24. At a later time, the potential applied to the bottom electrodes 24 is restored to its original potential so as to radially confine ions within the space 28.

As in the previously described embodiments, the exit region 6 from which ions are ejected from the drift cell 4 moves around the drift cell 4 along with the voltage gradient region 14. It will therefore be appreciated that the potentials applied to the bottom electrodes 24 will vary as the voltage gradient 14 moves around the drift cell 4 such that ions are ejected from the moving exit region 6. The bottom electrodes 24 around the drift cell 4 are typically all maintained at a relatively high potential relative to their corresponding side electrodes 26 so as to retain the ions in the space 28. Only the bottom electrodes 24 in the exit region 6 have their potentials dropped relative to their corresponding side electrodes 26 to a relatively low potential so as to eject ions. The exit region 6 moves around the drift cell 4 by travelling the low potential around the drift cell 4 such that the low potential is successively applied to the bottom electrodes 26 around the drift cell 4. The low potential is travelled around the drift cell 4 at a rate that is synchronized with the rate at which the voltage gradient travels around the drift cell 4, such that the exit region 6 is collocated with an end of the voltage gradient region 14.

Although the present invention has been described with reference to preferred embodiments, it will be understood by those skilled in the art that various changes in form and detail may be made without departing from the scope of the invention as set forth in the accompanying claims.

For example, the drift cell 4 need not be circular and may be any other shape provided that a continuous ion guiding path is formed. It is also contemplated that in less preferred embodiments the ion guiding path may not be continuous.

The invention claimed is:

1. A method of separating ions according to their ion mobility with:
an ion guide having a plurality of electrodes arranged to form an ion guiding path, said method comprising:
supplying RF voltages to at least some of said electrodes in order to confine ions within said ion guiding path;
maintaining a DC voltage gradient along at least a portion of a longitudinal axis of said ion guide, wherein said voltage gradient urges ions along the ion guide such that the ions separate according to their ion mobility as the ions pass along the ion guide, and wherein as time progresses the portion of the ion guide along which the DC voltage gradient is maintained is moved along the ion guide; and
providing an ion exit region which moves with respect to said ion guide such that ions exit said ion guide at different spatial locations at different times.

2. The method of claim 1, comprising moving the voltage gradient along the ion guide in a direction corresponding to the direction from high to low potential of the voltage gradient.

3. The method of claim 1, wherein the DC voltage gradient and exit region are moved along the ion guide with time such that the exit region remains at a low potential end of the voltage gradient so that ions exit the ion guide when the ions reach the low potential end of the voltage gradient.

4. The method of claim 1, comprising providing a potential barrier at a high potential end of the voltage gradient for preventing ions from exiting the voltage gradient region from the high potential end of the voltage gradient as the voltage gradient is moved along the ion guide.

5. The method of claim 4, comprising moving the voltage gradient along the ion guide at a first, high speed such that ions reside adjacent to the potential barrier and do not move down the voltage gradient, and then reducing the speed at which the voltage gradient is moved along the ion guide to a second, low speed such that ions move down the voltage gradient away from the potential barrier and separate according to ion mobility.

6. The method of claim 5, wherein when the voltage gradient is moving at said first, high speed, ions of high and low ion mobility are forced to reside adjacent to said potential barrier; and wherein when the voltage gradient is moving at said second, low speed, ions of low ion mobility are forced to reside adjacent to said potential barrier but ions of high mobility move down said voltage gradient and separate according to ion mobility.

7. The method of claim 6, further comprising reducing the speed at which the voltage gradient is moving around the ion guide to a third speed that is lower than said second speed such that said low mobility ions move down the voltage gradient and separate according to ion mobility.

8. The method of claim 6, wherein the ion guide forms a closed loop ion guiding path, and wherein the speed of the voltage gradient is selected such that said high or low mobility ions are driven multiple cycles around the ion guide whilst the ions travel down the voltage gradient.

9. The method of claim 1, comprising providing a potential barrier at a low potential end of the voltage gradient for preventing ions from exiting the voltage gradient region from the low potential end of the voltage gradient.

10. The method of claim 9, comprising maintaining the voltage gradient stationary or moving the voltage gradient along the ion guide at a first, low speed such that ions are forced in a direction towards the potential barrier by the voltage gradient, and then increasing the speed at which the voltage gradient is moved along the ion guide to a second, high speed such that ions move up the voltage gradient and begin to separate according to ion mobility.

11. The method of claim 10, wherein when the voltage gradient is stationary or moving at said first, low speed, ions of high and low ion mobility are forced to reside adjacent to said potential barrier; and when the voltage gradient is moving at said second, high speed, ions of high ion mobility are forced to reside adjacent to said potential barrier but ions of low mobility move up said voltage gradient towards a high potential end and separate according to ion mobility.

12. The method of claim 11, further comprising increasing the speed at which the voltage gradient is moved around the ion guide to a third speed that is higher than said second speed such that said high mobility ions move up the voltage gradient and begin to separate according to ion mobility.

13. The method of claim 11, wherein the ion guide forms a closed loop ion guiding path, and wherein the speed of the voltage gradient is selected such that said high or low mobility ions are driven multiple cycles around the ion guide whilst the ions travel up the voltage gradient.

14. The method of claim 10, wherein the exit region moves along the ion guide such that it is maintained at a high potential end of the voltage gradient, and wherein the ions move up the voltage gradient and exit the ion guide at the high potential end.

15. The method of claim 1, wherein the exit region is formed over a portion of said ion guide by modifying a voltage supplied to one or more of said electrodes such that ions are not confined by said one or more electrodes in the exit region.

16. The method of claim 15, wherein a first potential is applied to said electrodes outside of said exit region in order to radially confine ions and a second, different potential is applied to one or more electrodes inside the exit region in order to allow or cause ions to exit the ion guide.

17. The method of claim 16, wherein the second potential is sequentially applied to successive electrodes along the ion guide such that the exit region moves along the ion guide.

18. The method of claim 1, wherein said plurality of electrodes comprise apertured electrodes, the electrodes and apertures of the electrodes being aligned so as to guide ions through the apertures and around the ion guide.

19. The method of claim 18, wherein the aperture in each apertured electrode is a slot formed into the electrode from an edge thereof, such that the slot has an open end at an edge of the electrode.

20. The method of claim 19, comprising providing at least one gate electrode adjacent to the open end of each slot, and applying a first potential to said gate electrode in order to prevent ions exiting the open end of the slot in regions of the ion guide outside of the exit region; and applying a second potential to said gate electrode in order to allow or cause ions to exit the open end of the slot in regions of the ion guide inside of the exit region.

21. The method of claim 19, wherein the electrodes are arranged such that at least a portion of the ion guiding path is curved and so has a radius of curvature, wherein each slot has its minimum dimension parallel with said radius and its maximum dimension perpendicular to said radius.

22. The method of claim 1, wherein the ion guide forms a closed loop ion guiding path, and wherein the voltage gradient and exit region move around the ion guide.

23. A method of mass spectrometry comprising separating ions according to a method as claimed in claim 1.

24. The method of claim 1, comprising moving said ion exit region with respect to said ion guide along said longitudinal axis of said ion guide such that ions exit said ion guide at different spatial locations along said longitudinal axis of said ion guide at different times.

25. The method of claim 1, wherein:
the ions separate according to their ion mobility along said longitudinal axis of said ion guide; and
the ions, the ion exit region and the portion of the ion guide along which the DC voltage gradient is maintained move along said longitudinal axis of said ion guide in the same direction.

26. The method of claim 1, wherein the ions that exit said ion guide at different spatial locations at different times exit said ion guide at different spatial locations at different times during a single ion mobility separation experiment.

27. A method of separating ions according to their ion mobility with a circular or closed loop RF ion guide, said method comprising:
causing ions to undergo one or more cycles around said ion guide;
retaining said ions radially within said ion guide by a pseudo-potential voltage;
maintaining an axial DC voltage gradient along a portion of said ion guide; and
providing a rotating ion entrance/exit port which rotates with respect to said ion guide.

28. The method of claim 27, further comprising moving said ion entrance/exit port with respect to said ion guide along a longitudinal axis of said ion guide such that ions exit said ion guide at different spatial locations along said longitudinal axis of said ion guide at different times.

29. The method of claim 27, wherein:
the ions separate according to their ion mobility along a longitudinal axis of said ion guide; and
the ions, the ion entrance/exit port and the axial DC voltage gradient move along said longitudinal axis of said ion guide in the same direction.

30. An ion mobility separator comprising:
an ion guide having a plurality of electrodes arranged to form an ion guiding path;
a device arranged and adapted to supply RF voltages to at least some of said electrodes in order to confine ions within said ion guiding path;
a device arranged and adapted to maintain a DC voltage gradient along at least a portion of a longitudinal axis of said ion guide, such that as time progresses the portion of the ion guide along which the DC voltage gradient is maintained is moved along the ion guide; and
a device arranged and adapted to provide an ion exit region which moves with respect to said ion guide such that, in use, ions exit said ion guide at different spatial locations at different times.

31. An ion mobility separator as claimed in claim 30 wherein said ion guide forms a closed loop ion guiding path.

32. An ion mobility separator comprising:
a circular or closed loop RF ion guide, wherein in use ions are caused to undergo one or more cycles around said ion guide and are retained radially within said ion guide by a pseudo-potential voltage;
a device arranged and adapted to maintain an axial DC voltage gradient along a portion of said ion guide; and
an ion entrance/exit port which rotates, in use, with respect to said ion guide.

33. An ion mobility separator as claimed in claim 32, wherein said axial DC voltage gradient progresses in use around said ion guide.

34. An ion mobility separator as claimed in claim 32, wherein said axial DC voltage gradient has a DC potential barrier towards a high potential end of said voltage gradient, said DC potential barrier preventing ions from passing axially across said DC potential barrier.

35. An ion mobility separator as claimed in claim 32, wherein said ion guide comprises a plurality of electrodes each having an elongated aperture through which ions are transmitted in use.

36. An ion mobility separator as claimed in claim 32, wherein said ion entrance/exit port moves with respect to said ion guide along a longitudinal axis of said ion guide such that ions exit said ion guide at different spatial locations along said longitudinal axis of said ion guide at different times.

* * * * *